United States Patent [19]

Wellerfors

[11] Patent Number: 4,475,411

[45] Date of Patent: Oct. 9, 1984

[54] SAMPLING APPARATUS

[75] Inventor: Hans Wellerfors, Hägersten, Sweden

[73] Assignee: Coulter Electronics Limited, Luton, England

[21] Appl. No.: 359,565

[22] Filed: Mar. 18, 1982

[30] Foreign Application Priority Data

Mar. 20, 1981 [SE] Sweden ............................. 8101788

[51] Int. Cl.³ .......................................... G01N 35/02
[52] U.S. Cl. .................................. 73/864.24; 422/64
[58] Field of Search ..................... 422/63, 64, 67, 104, 422/100, 72; 73/864.24, 864.22, 864.21

[56] References Cited

U.S. PATENT DOCUMENTS

| | | | |
|---|---|---|---|
| 3,479,880 | 11/1969 | Mutter et al. | 73/864.21 |
| 3,614,434 | 10/1971 | Horwitz et al. | 422/64 |
| 4,063,460 | 12/1977 | Svensson | 422/100 |
| 4,217,780 | 8/1980 | O'Connell et al. | 73/864.22 |

*Primary Examiner*—Gerald Goldberg
*Assistant Examiner*—John E. Chapman, Jr.
*Attorney, Agent, or Firm*—Silverman, Cass & Singer, Ltd.

[57] ABSTRACT

Apparatus for taking a sample of liquid from each of a plurality of containers. Blood or similar settling liquids requiring continuous mixing are sampled for subsequent analysis from test tubes closed by rubber or plastic plugs. The test tubes are mounted along the periphery of a rotatable cassette, which is drivingly connected to a motor via gearing, a clutch and a brake, in such a manner, that the cassette rotates in order to maintain the liquids in the test tubes thoroughly mixed. The cassette is capable of stopping instantaneously when the clutch is disengaged. The cassette is locked in accurate position in front of a sampling needle by operation of the brake. The brake operates when a signal from an analysis instrument orders an electronic counter to determine the identity of the test tube to be selected and the cassette is stopped. Immediately, a pneumatic cylinder is operated to lower an arm fixing the selected test tube. A second pneumatic cylinder also is operated to lower the sampling needle to perforate the closure. The sampling needle is lowered to a definite level and, after having arrived at this position, effects a signal to the analysis instrument. Responsive to said signal, a definite liquid amount is drawn through the sampling needle, the needle withdrawn from the tube, the arm lifted, the brake disengaged, the clutch engaged and the cassette resumes its rotation.

12 Claims, 3 Drawing Figures

SAMPLING APPARATUS

This invention relates to apparatus for taking a sample quantity of liquid from each of a plurality of containers.

Where the liquid is a liquid suspension, for example blood, which is subject to sedimentation or separation of its components on standing, difficulty arises in obtaining a sample which is representative of the liquid suspension as a whole.

Blood mixing machines are known in which an operator can place one or more containers for agitation prior to removal of the containers for sampling. Such machines are disadvantageous because of the need for the operator to load and unload the mixing machine in addition to dealing with the taking of samples.

British patent specification No. 1,237,805 describes a blood analyser comprising a turntable containing a plurality of loosely held receptacle holders into which individual specimen cups loosely fit. The cups are oscillated by means of magnetic pins, extending from the base of the receptacle holders, and a rotating magnetic field in an attempt to keep the blood samples homogeneous. One major disadvantage of this and similar machines is that the use of open containers on a turntable exposes the operator to the risk of contamination and infection from the blood samples.

U.S. Pat. No. 4,120,662 describes an apparatus for obtaining samples from a series of closed containers in which a pair of parallel feed screws move the closed containers along a predetermined path to a sampling station. In a mixing mode, the feed screws impart motion to the closed containers while they are moved along the path in an attempt to obtain a substantially uniform distribution of the particles contained in the containers. This machine imparts a mixing motion to the containers individually but the effectiveness of mixing is limited by the motion the feed screws are capable of imparting to the containers. Furthermore, the containers have to be inserted individually into the feed screws and the order in which they are sampled is necessarily the order in which they lie in the feed screws.

The present invention provides:

Apparatus for taking a sample of liquid from each of a plurality of containers, comprising a receptacle so mounted as to be readily removable from the apparatus and capable of receiving and holding a plurality of said containers, means on the apparatus for receiving and supporting the receptacle and so moving it as to cause the containers held thereon to follow a defined path to a sampling station along the path and to be inverted in moving along said path to cause agitation of liquid in the containers, means for arresting a container at the sampling station with respect to a sampling means, and means for actuating the sampling means to cause it to withdraw a sample from the container.

Preferably, the receptacle is a circular carrier having means for receiving and locating the plurality of containers thereon spaced circumferentially round said carrier, and the receiving and supporting means is arranged to rotate the carrier so that the containers move generally in a plane at a substantial angle to the horizontal. Advantageously, said angle is not less than 30°.

Preferably, the carrier is capable of receiving elongate containers having an access opening at one end. The containers are located approximately in a common plane. The carrier is rotated so that the containers follow a defined path of movement lying in said plane.

Preferably, the carrier is constructed to mount the containers disposed approximately radially relative to the axis of the carrier with the access ends opening outwardly of the circumference of the carrier.

Preferably the carrier is arranged to receive and locate said elongate containers each at an angle to the general plane of said carrier.

The present invention also provides apparatus for taking a sample from each of a plurality of test tubes distributed about the periphery of a cassette with the long axes thereof lying in a generally common vertical plane. The cassette is rotatable in the vertical plane and is drivingly connected to a motor via a gear set, clutch and brake. The cassette is rotated to mix thoroughly the liquids within the test tubes. The cassette is capable of being stopped by disengagement of the clutch. The cassette then is locked in accurate position in front of a sampling needle by the brake. The locking occurs when a signal from an analysis instrument orders an electronic counting mechanism to calculate the test tube in question and stop the cassette. A pneumatic cylinder lowers an arm holding a selected one of the test tubes. A second pneumatic cylinder also lowers a sampling needle and thereby perforates the closure of the test tube, the sampling needle being lowered to a definite position. After the needle has reached said position, a signal is directed to the analysis instrument, represented diagrammatically in FIG. 1 by reference character 200 causing the needle to withdraw a predetermined amount of liquid sample from the tube, and further causes the sampling needle to be raised, the arm to be lifted, the brake released, the clutch engaged that the cassette again rotated.

The cassette preferably is cylindrical, with a circumferential surface parallel with the axis of rotation of the cassette, and means are provided to mount the containers, test tubes arranged radially relative to the cassette with the access ends extending outward from the circumferential surface.

The mixing can be still more efficient when the circumferential peripheral surface entirely or partially is beveled, preferably with a bevel angle of 45°, and the test tubes are mounted within receiving passageways formed in the beveled surface and which are each directed at an angle of 45° to the axis of rotation.

The same effective mixing can be obtained, when the circumferential surface of the cassette is parallel to the drive axle and the test tubes are directed inward toward center axis of the cassette and the angle between the longitudinal axis of the test tubes and the axis of rotation of the cassette is 90°, by inclining the entire sample carrier so that the angle of the cassette to the horizontal plane is not smaller than about 30°. If the cassette is arranged so that the cassette is disposed too horizontally, the withdrawal of the liquid sample as well as the mixing of said samples will be unreliable.

Preferably, the cassette is mounted on one end of an axle. An electromagnetic brake is located at the opposite end of the axle. The electromagnetic brake co-operates with an electromagnetic clutch. This arrangement ensures instantaneous stopping the rotation of the cassette in accurate position from a rotation speed of about 15–20 rpm when the electronic counting mechanism has ordered said stop. The analysis instrument directs a signal to the electronic counting mechanism, for example, implying that the analysis instrument is ready to receive the next sample.

Preferably, the sampling needle comprises two tubes, one for the sample liquid and one for permitting air to enter the test tube to prevent vacuum arising within the test tube.

Referring now to the drawings.

Figure 1:
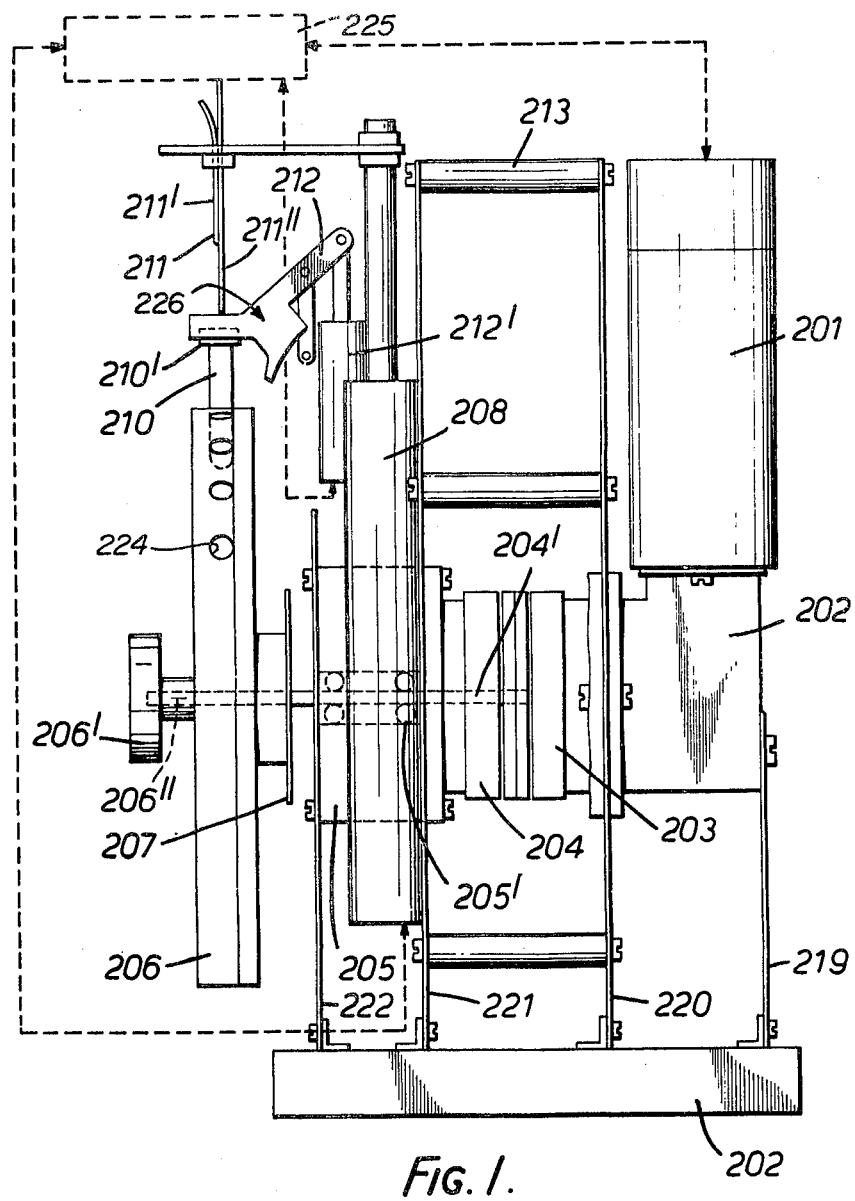
FIG. 1 is a schematic side view of the apparatus.
Figures 2, 3:
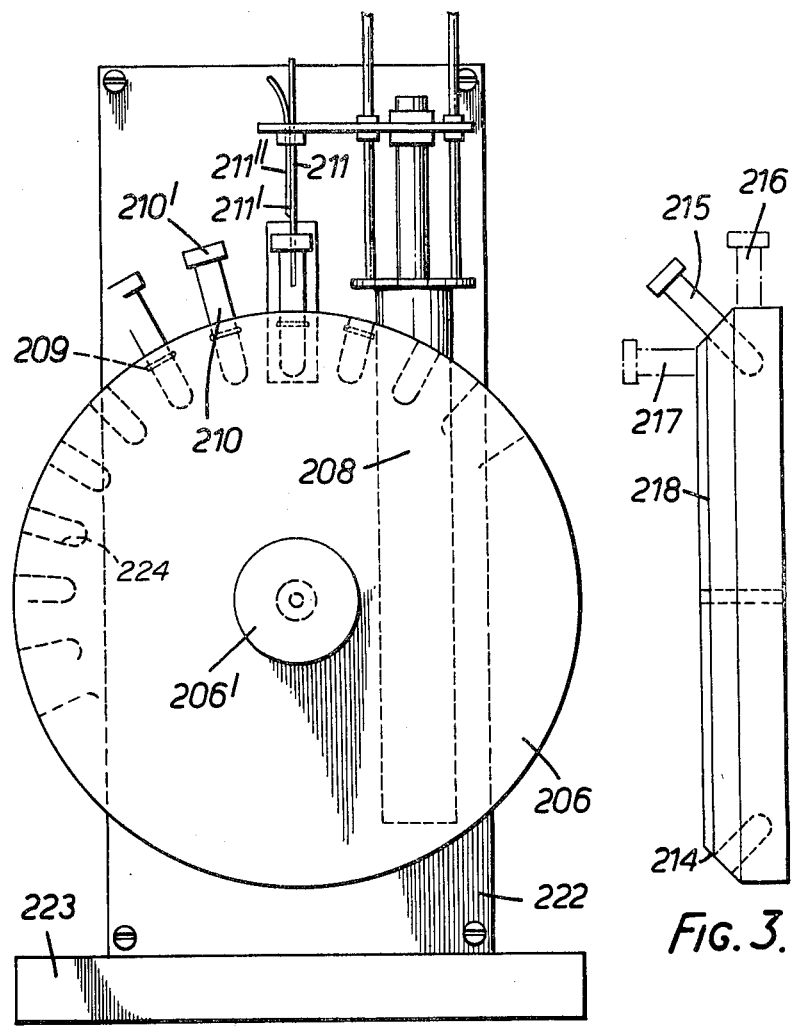
FIG. 2 is a schematic front view of the apparatus.
FIG. 3 is a side view of a cassette used in the apparatus and illustrates different forms the cassette can take.

Referring to FIGS. 1 to 3, a sampling apparatus is illustrated for mixing and sampling blood or similar settling liquids requiring continuous mixing. The blood or other liquid for subsequent analysis is contained in test tubes 210 the upper open ends of which are closed by closures 210' formed of soft rubber or plastic plugs 210' for example. The test tubes 210 are mounted along the pheriphery of an easily exchangeable cassette 206 constructed to hold twenty-five test tubes. The cassette is circular in configuration. The test tubes are mounted radially in the cassette and extend outwardly from the circumferential surface thereof.

The sampling apparatus has a base 223, support members 219, 220, 221 and 222, and spacers 213.

The test tubes 210 are retained in the cassette 206 in elongate cylindrical recesses 224 drilled in the cassette and which correspond to the outer diameter of the test tubes plus a small clearance. A groove of semi-circular shape is formed in the inner circumferential surface of the passageways so that the grooves are tangent to the said surface. An O-ring 209 is inserted into each groove and has a thickness slightly exceeding the width of the groove. As a result, the O-ring enters partially into the cylindrical recess 224 by one or some tenths of a millimeter. This is sufficient for holding the test tubes in position during rotation of the cassette 206.

The cassette 206 is connected to be driven by a motor 201, running at 1400 revolutions per minute, by way of a reduction gear 202 with reduction ratio 75:1, an electromagnetic clutch 203 and an electromagnetic brake 204. The output shaft of the reduction gear 202 runs at 18.5 revolutions per minute and the electromagnetic clutch 203 connected to said shaft transfers the rotary movement to an axle 204' and the electromagnetic brake 204.

The axle 204' is mounted by ball bearings 205' within associated bearing box 205. At the other end of the axle 204' the cassette 206 is mounted secured to the opposite end of axle 204' by means of an internally threaded wheel or knob 206'.

A guide pin 206" or a wedge on the drive shaft are provided to ensure that the cassette 206 can be mounted on the drive shaft only in a given position.

The cassette 206 is rotated at constant speed for maintaining the sample liquids thoroughly mixed but is capable of being stopped instantaneously by operation of the clutch 203 to separate the drive means from the drive cassette and locking of the cassette in accurate position in front of a sampling needle 211 by means of the brake 204. The rotation of the cassette 206 is stopped when a signal from an analysis instrument associated with the sampling apparatus orders an electronic counting mechanism of said sampling apparatus to determine the position of a test tube in question and stop the cassette accordingly. The cassette is stopped for only a short time so that the analysis instrument can cause new sample to be withdrawn by the sampling apparatus.

The selected test tube containing the liquid to be sampled is stopped directly in front of the sampling needle. The needle is lowered after the fixing arm is lowered, said needle perforating the closure cap of the test tube, the analysis instrument effecting the withdrawal of a required volume of sample liquid.

When the cassette is stopped, an arm 212 is immediately lowered by operation of pneumatic cylinder 212' to hold the selected test tube in position. The sampling needle 211 is lowered by operation of a second pneumatic cylinder 208 thereby to perforate the selected closure 210' of the tube. The sampling needle 211 is lowered to a definite position and, after this position has been reached a signal is sent to the analysis instrument which causes withdrawal of a predetermined volume of liquid. The sampling needle 211 then is raised, the arm 212 lifted, the brake 204 released and the clutch 203 engages so that the cassette 206 once again begins to rotate.

The pneumatic cylinder 212' controls the movement of the arm 212, which in lowered position has the purpose of holding the slected test tube in position. The arm in raised position functions to hold a drain cup 226 below the sampling needle and said needle is flushed clean.

The second pneumatic cylinder 208 manages the up and down movement of the sampling needle.

An electronic 25-counting mechanism (not shown) with associated screen or code disc 207 is mounted on the axle of the cassette 206 and indicates the number of the test tube which is located beneath the sampling needle 211. The pneumatic cylinder 208 effects the upward and downward movement of the sampling needle 211. The sampling needle consists of two narrow tubes 211' and 211". When the needle has been pressed down through the closure of a tube and has arrived at a certain level, the analysis instrument 225 shown diagrammatically in FIG. 1, causes sample liquid to be drawn into the tube 211'. The tube 211" also concurrently penetrates the closure 210' to permit air to enter the test tube in order to prevent a vacuum condition from arising therein, which condition would render the withdrawal of liquid more difficult or slower.

The lower end of the tube 211" penetrates fully through the closure 210' of the test tube and terminates interior of the test tube so that the lower opening of the tube 211' of the immersed sampling being entirely free of the closure 210'.

The second pneumatic cylinder 212' which effects movement of the arm 212 has two functions, namely (i) to hold and maintain the test tube in position in the cassette when the sampling needle 211 is being drawn out of closure 210' and (ii) to position a drain cup below the sampling needle 211 while it is flushed clean. A vacuum suction device is connected to the drain cup for sucking away the mixture of flushing liquid and sample liquid.

When the sample needle 211 has been drawn upward and the fixing arm 212 is in its upper position the brake 204 is released. The clutch 203 is reengaged and starts immediately taking along the cassette and resulting in the cassette assuming its previous speed, 18.5 revolutions per minute, for example.

FIG. 3 illustrates a modified embodiment of the invention wherein the cassette is provided with a beveled circumferential surface 214 in which the test tubes are positioned obliquely in the position represented by resulting 215. The resulting mixing obtained (of settling liquids, for example blood) is considered to be improved over that obtained in position 216, considerably improved over the mixing and above all obtained when the tubes are arranged in position 217. One disadvantage of the modified cassette is the resulting increased thickness required. For position 215, the O-ring advantageously lies beneath the mouth of the test-tube holes.

The sampling apparatus described by way of example need not, of course, be constructed in the way described, but can be varied in several ways, for example a stepping motor with braked rotor can be used.

What I claim is:

1. Apparatus for taking a sample of liquid from each of a plurality of sealed containers each having pierceable closures, comprising a carrier, container receiving means in said carrier for receiving and holding a plurality of said sealed containers, means on the apparatus for supporting said carrier for rotation about the central axis thereof in a plane generally normal thereto and drive means for said carrier to cause the containers held thereby to follow a defined path to a sampling station disposed along the path and each container being inverted at least once during its movement along said path with movement of the carrier whereby to cause agitation of liquid in the containers, sampling means disposed at the sampling station, means for arresting a container at the sampling station with respect to said sampling means, and means for actuating said sampling means to effect withdrawal of a sample from the container, said sampling means including piercing needle means arranged at said sampling station for selective operation to pierce the closure of the sealed container when the container is stopped at the sampling station whereby to advance said needle means into the container and means for holding the container during withdrawal of sample therefrom.

2. Apparatus as claimed in claim 1, wherein said carrier is circular in configuration, said container receiving means being spaced circumferentially, said carrier being moved generally in a rotational plane which is at a substantial angle relative to the horizontal plane.

3. Apparatus as claimed in claim 2, wherein the said angle is not less than 30°.

4. Apparatus as claimed in claims 2 or 3, wherein the carrier is capable of receiving elongate containers each having an access end outwardly facing relative to the periphery of said carrier, said containers located approximately in a common plane, said carrier being rotatable to cause the containers therein to follow a defined path of movement which lies in a plane taken generally normal to the axis of rotation of the carrier.

5. Apparatus as claimed in claims 1 or 2 wherein the containers have an elongate configuration, said containers being located each angularly directed relative to the plane in which said carrier rotates, the angle being no greater than about 45°.

6. Apparatus for mixing and sampling for subsequent analysis blood or similar settling liquids requiring continuous mixing in test tubes sealingly closed by pierceable resilient plugs comprising: a rotatable cassete; means for holding and retaining the test tubes to dispose said test tubes axially normal to the rotational axis of said cassette with the plugs facing outwardly thereof along the periphery of said rotatable cassette; drive means coupled to said cassette for rotating said cassette about its axis; said drive means including motor, a clutch and a brake, rotation of said cassette causing the liquids in the test tubes to be thoroughly mixed, said clutch being operable to separate the drive means from the driven cassette and said brake being applied to stop the rotation of the cassette at a selected position and to lock said cassette at said position; sampling needle means including a sampling needle at a sampling location; means for selecting one of said test tubes and generating a stop signal, said drive means being responsive to said stop signal to stop said cassette; means for holding the selected test tube at the sampling location during sampling; means for advancing said sampling needle through said plug to enter said liquid sufficiently to enable withdrawal of a definitive amount of liquid; means generating and directing a liquid withdrawal signal operative to effect withdrawal of the definitive amount of liquid and to retract the sampling needle from the plug, release the brake, reengage the clutch and resume rotation of the cassette.

7. Apparatus as claimed in claim 6, wherein the cassette has a cylindrical configuration including an outer circumferential surface which is parallel with the axis of rotation of the cassette, said mounting and retaining means being formed radially outwardly extending relative the axis of rotation and within said cassette for receiving therein test tubes mounted radially relative to the said axis of rotation, said test tubes having the plugs accessible and outwardly extending relative to said circumferential surface.

8. Apparatus as claimed in claim 6, wherein the cassette has a circular configuration including a circumferential surface, said circumferential surface including a portion at least partially beveled at least at an angle of about 45° and said mounting means for said test tubes formed in said cassette and opening to said partially beveled surface at an angle of about 45° relative to the axis of rotation of said cassette.

9. Apparatus as claimed in claim 6, wherein the cassette is located in a plane which deviates from the horizontal plane by an angle not less than 30°.

10. Apparatus as claimed in claim 6, wherein the cassette is removably replaceably mounted to facilitate exchange of one cassette for another like cassette.

11. Apparatus as claimed in claim 6, wherein the clutch and the brake are of an electromagnetic type.

12. Apparatus as claimed in claim 6, wherein the sampling needle comprises at least two tubes, one tube for receiving the sample liquid, and one tube capable of allowing air to enter the test tube in order to prevent vacuum from arising in the test tube.

* * * * *